United States Patent [19]

Shigematsu et al.

[11] Patent Number: 5,427,950
[45] Date of Patent: Jun. 27, 1995

[54] METHOD FOR RADIOACTIVITY MEASUREMENT, PROCESS FOR PREPARING SAMPLE AND DEVICE THEREFOR

[75] Inventors: Akiyo Shigematsu; Naomi Motoji; Yasuko Niikura; Yuko Shiina; Yasuhiko Hatori; Mitsunobu Okuyama, all of Chiba, Japan

[73] Assignee: Kabushiki Kaisha Seitai Kagaku Kankyusho, Chiba, Japan

[21] Appl. No.: 3,512

[22] Filed: Jan. 12, 1993

[30] Foreign Application Priority Data

Jan. 18, 1992 [JP] Japan .................... 4-027293
May 20, 1992 [JP] Japan .................... 4-152850
Oct. 30, 1992 [JP] Japan .................... 4-316482

[51] Int. Cl.$^6$ .................... G01N 23/00; G01N 1/00
[52] U.S. Cl. .................... 436/57; 250/358.1; 250/361 R; 250/443.1; 436/174; 436/181
[58] Field of Search .................... 436/57, 58, 174, 181; 422/99; 250/443.1, 424, 432 R, 358.1, 361 R, 364; 62/341, 345; 100/93 P

[56] References Cited

U.S. PATENT DOCUMENTS

| 3,875,012 | 4/1975 | Dorn et al. | 435/30 |
|---|---|---|---|
| 3,898,023 | 8/1975 | Faust | 425/110 |
| 4,387,166 | 6/1983 | Maes | 436/517 |
| 4,565,073 | 1/1986 | Lavender | 62/341 |
| 4,578,963 | 4/1986 | Sitte | 62/514 R |
| 4,621,196 | 11/1986 | Arakawa | 250/483.1 |
| 4,690,897 | 9/1987 | Squires et al. | 435/172.3 |
| 4,703,177 | 10/1987 | Vieth | 250/327.2 |
| 4,745,764 | 5/1988 | Sitte et al. | 62/78 |
| 4,753,082 | 6/1988 | Sudo et al. | 62/341 |
| 4,891,185 | 1/1990 | Goldin | 436/57 |
| 4,907,421 | 3/1990 | Battistella | 62/341 |
| 5,044,165 | 9/1991 | Linner et al. | 62/55.5 |
| 5,132,089 | 7/1992 | Lightfoot | 422/99 |
| 5,143,850 | 9/1992 | Pentoney et al. | 436/57 |

FOREIGN PATENT DOCUMENTS

0397600A1 11/1990 European Pat. Off.
3625695A1 11/1988 Germany.

OTHER PUBLICATIONS

Database WPI, Derwent Publications Ltd., London, GB; AN91-301355 (Lengd Radiation Hyg), Apr. 1991.
Database WPI, Derwent Publications Ltd., London, GB; AN 81-79308D (As Geor Phys Inst), Feb. 1981.
Soviet Patents Abstracts, Derwent Publications Ltd., London, GB; AN 91-213802/29 (Lengd Radiation Hyg), Sep. 1991.

*Primary Examiner*—Robert J. Warden
*Assistant Examiner*—Robert Carpenter
*Attorney, Agent, or Firm*—Jones, Tullar & Cooper

[57] ABSTRACT

A method of quantitative measurement of a very small amount of low-energy beta radioactivity in a biological sample, a process for preparing samples and a device therefore, which require no large-scaled equipment and no labor for sample preparation, measurement, correction of the measured values and treatment of waste solution after measurement. The method comprises: forming a solid, liquid or liquefied biological sample containing a radioactive substance so as to have a substantially uniform and predetermined thickness; freezing or solidifying the sample and measuring the radioactivity thereof.

15 Claims, 14 Drawing Sheets

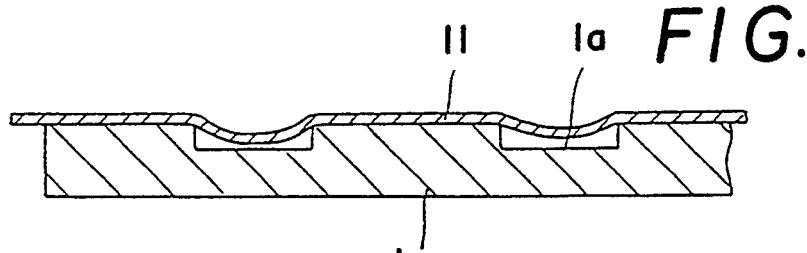
FIG. 9(A)
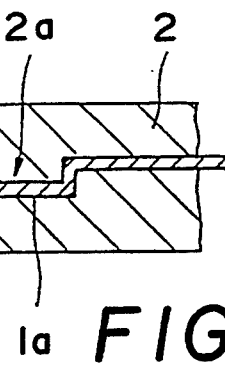
FIG. 9(B)
FIG. 9(C)
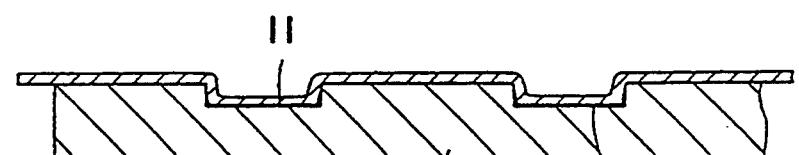
FIG. 9(D)
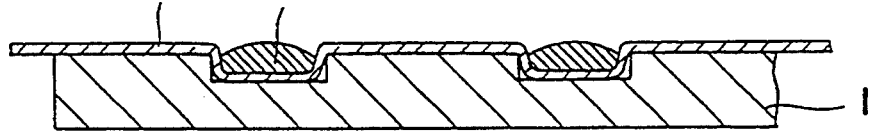
FIG. 9(E)
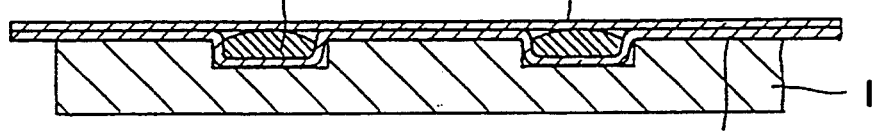
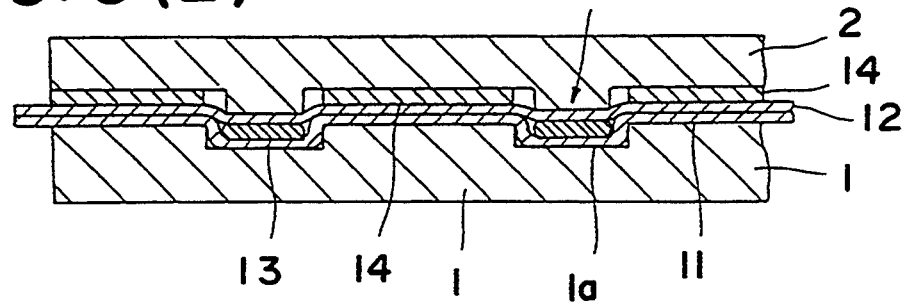
FIG. 9(F)

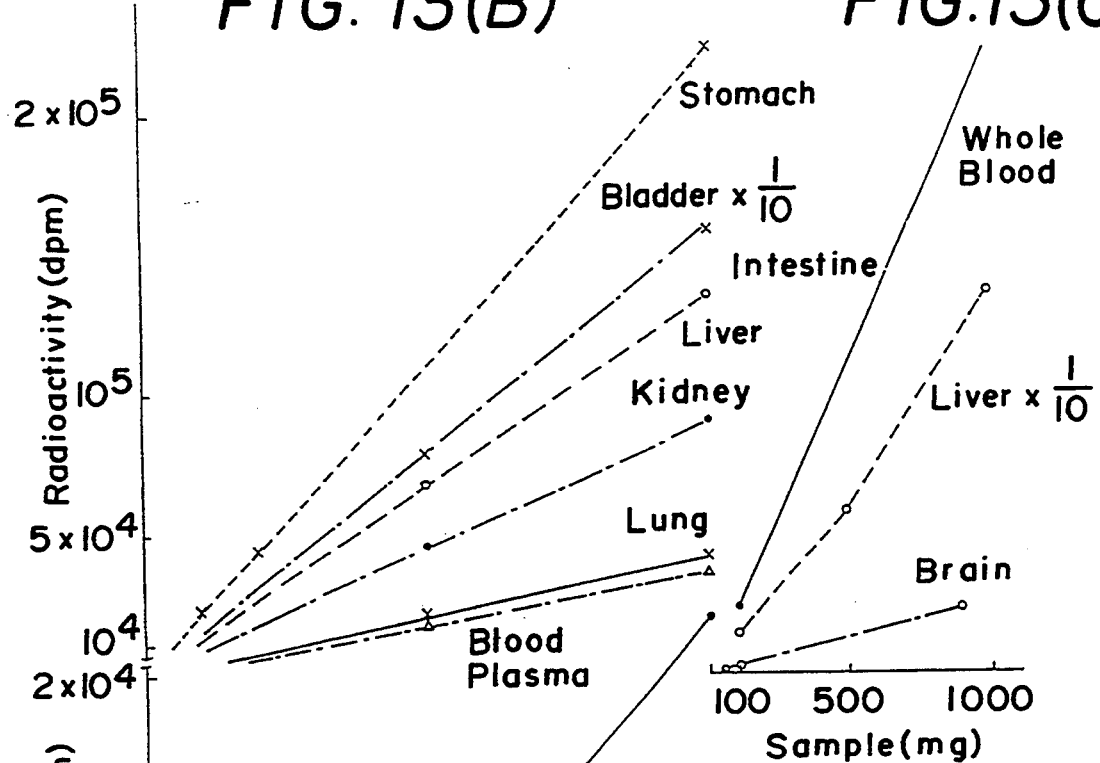
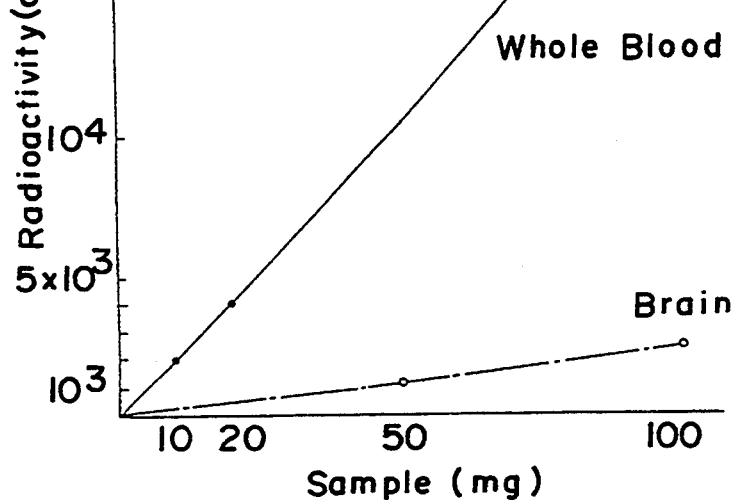
FIG. 13(B)
FIG. 13(C)
FIG. 13(A)

METHOD FOR RADIOACTIVITY MEASUREMENT, PROCESS FOR PREPARING SAMPLE AND DEVICE THEREFOR

FIELD OF THE INVENTION

The present invention relates to a method for radioactivity measurement of high sensitivity and reliability, without requiring large-scale equipment and labor for measurement and for treatment of waste solution after measurement, and also to a process for preparing samples for radiation measurement and a device therefor.

BACKGROUND OF THE INVENTION

Liquid scintillation has been mainly employed for measurement of radiation from a low-energy beta emitter (for example, $^{14}C$, $^3H$) contained in an organic sample such as a biological sample, etc. The liquid scintillation wherein the sample itself is dissolved or dispersed in the liquid scintillation medium can measure even low-energy beta radiation with high sensitivity.

In an experiment of tracer for biological tissues, etc., the sample is frozen to prevent migration of water-soluble or volatile labeled substance (elution from the sample, diffusion in the sample, etc.) and a thin section is prepared while the sample is frozen, which is directly lyophilized in a vacuum and its radioactivity is measured.

In the known liquid scintillation method, however, the preparation of the scintillator solution containing radioactive samples is troublesome and the solution should be treated after radiation measurement to prevent environmental contamination.

For treatment of the scintillator solution after measurement, there are two methods, that is, a method wherein the solution is directly incinerated and a method wherein only the combustibles are incinerated after pretreatment. The former has serious problems, that is, the presence of noncombustibles, scattering of radioactivity, etc. which are obstructions to practical application.

As the pretreatment, a method has been employed wherein the waste solution is distilled and the distillate, optionally combined with the residual solution after filtration, and incinerated with liquid fuel such as kerosene. The method, however, requires a complicated and expensive apparatus.

As other defects of the liquid scintillation method, a large number of substances which act as quenchers for the scintillator (hereinafter simply referred to as quencher) exist in the biological sample which contains a large amount of biological components other than the labeled substances, making for complicated effects. Accordingly, it is difficult to quantitatively measure a very small amount of radioactivity by the liquid scintillation method. The effect of such quenchers may be removed to some extent by compensation for the quenching which requires an additional apparatus, labor and time.

The method of lyophilizing the sample, wherein the preparation of the sample section and vacuum lyophilization are carried out at low temperature, requires a large-scale equipment, much labor and time.

SUMMARY OF THE INVENTION

Accordingly, an object of the present invention is to provide a method for quantitative measurement of a very small amount of the low-energy beta-radioactivity in a biological sample without requiring large-scale equipment, labor for sample preparation before measurement, correction of the data and treatment of waste solution after measurement.

Moreover, another object of the present invention is to provide a method for quantitative measurement of a very small amount of radioactivity in a biological sample containing a large number of quenchers.

To attain the above objects, the method for radiation measurement of the present invention comprises preparing a sample of substantially uniform thickness by a method, for example, a method wherein a solid, liquid or liquefied biological sample containing a radioactive substance is spread between two rigid planes, such as two flat surfaces of rigid bodies, separated by a predetermined distance, freezing or solidifying the sample and measuring radioactivity of such frozen or solidified sample while it contains substantially water.

Still another object of the present invention is to provide a method and a device for preparation of samples for quantitative measurement of the low-energy beta-radiation in a biological sample without requiring large-scale equipment and labor for sample preparation before measurement and for treatment of waste solution after measurement.

In the present invention, to realize the above method, a biological sample containing a radioactive substance is frozen, uniformly pressed and crushed between two rigid planes kept at a fixed temperature lower than the freezing point, compressed to give a thin section of substantially uniform thickness which is used as a sample for radiation measurement.

The device to attain the above object according to the present invention comprises means to uniformly press and crush the frozen biological sample containing a radioactive substance consisting of two opposite rigid planes which can be separated with a fixed space to compress the sample to a substantially uniform thickness and means to keep the rigid planes at a fixed temperature.

As the biological sample, any of solid, semisolid (e.g., gel), liquid or the like may be used. Since samples are taken from living bodies, they contain usually water and therefore solid samples are soft. A solid or semisolid biological sample can be pressed between the two rigid planes to a substantially uniform and fixed thickness. Alternatively, a solid or semisolid biological sample may be liquefied. It is convenient to use chemical methods for liquefaction. For example, the biological sample can be liquefied using a strong alkaline solution of sufficient concentration.

The two rigid planes used to prepare a biological sample of a substantially uniform thickness between them may be made of either metal or non-metal material, for example, iron, ferro-alloy, copper alloy, aluminum, stone, glass, pottery, plastic, etc. Among them, metal with good heat conductivity and relatively great specific gravity, for example, stainless steel is preferred for solidification by cooling or freezing. The two rigid bodies may be made of different materials.

It is preferable to hold the two rigid planes separated with a fixed space corresponding to the thickness of the sample using an appropriate means to spread the sample to a fixed thickness between the two rigid planes. For example, at least either of the rigid bodies is provided with at least three protrusions of a fixed height, only the area to contain the sample is depressed, or a member of a fixed thickness (spacer) is sandwiched between the two rigid bodies, leaving a space for a sample. To prevent radioactive contamination, the surface of the rigid bodies may be covered, for example, with thin plastic films. The thickness of the plastic film, etc. is as thin as possible considering absorption of radiation, especially low energy beta ray radiation.

To form the solid biological sample in a predetermined thickness, it is pressed between the two rigid planes under an appropriate pressure. The required pressure varies depending on the softness of the biological sample. Generally, a pressure around 5 g/cm² is required. It is difficult to press a hard sample such as a bone, a tooth, a tusk, a horn, a ligament, etc. between the two rigid planes to a fixed thickness. Accordingly, such samples should be ground by other means and treated, for example, liquefied. A slight pressure Will suffice to spread the liquid or liquefied sample to a fixed thickness.

To solidify the biological sample, a method which comprises adding gelatin etc. to the liquid or liquefied sample, cooling the resultant on the surface of the rigid body for solidification is employed. The solid may be further frozen. It is more preferable to simply freeze the sample rather than to solidify it because the frozen sample has a smooth surface, that is, it has a uniform thickness. The surfaces of the two rigid planes are kept at a temperature below the freezing point, for example, at −50 ° C., to freeze the sample. After freezing, the temperature of the sample is preferably raised nearly to the freezing point (e.g., −10° C.) so as to prevent an increase of unevenness of the surface due to growth of the ice crystals by refreezing.

The frozen or simply solidified biological sample is used for radiation measurement. The important feature of the present invention is to measure radioactivity of the frozen or solidified sample while it contains substantially water. To measure radioactivity, either a physical or chemical method may be employed. For example, a Geiger-Müller counter, a proportional counter, a scintillation counter, a semiconductor detector, an imaging plate utilizing photostimulated luminescence (PSL, hereafter), silver salt photosensitive material or the like may be employed.

Most of the biological samples are liquid or amorphous solid samples with elasticity, which contains water as a main ingredient. The sample may lose elasticity and be plasticized upon freezing so that it can be compressed, crushed and extended to a thin section while it is frozen. Such a thin section is used for radiation measurement while it is frozen.

Where a previously frozen sample is used, pressing is carried out by applying a force sufficient to grind the frozen sample to form a thin tablet. Generally, a pressure of 100 g/cm² or more is required. When there is no means to control the thickness of the thin section, it is desirable to apply a uniform force to the sample to compress the sample to a uniform thickness between the surfaces of the two rigid planes. In this case, temperature should be strictly controlled.

The device of the present invention uniformly presses and crushes the frozen biological sample between the opposite two rigid planes placed with a fixed space to give a thin section with a uniform thickness. To keep the biological sample in a frozen state, the surfaces of the rigid bodies constituting the two planes may be kept at a fixed temperature.

DESCRIPTION OF THE DRAWINGS

FIG. 9(A) to (E) are explanatory drawings showing procedures to prepare samples for radiation measurement using a device of the present invention.

FIG. 13(A–C) is a graph showing a result of the measurement of radioactivity according to the present invention.

DETAILED DESCRIPTION OF THE INVENTION

The present invention will be illustrated in detail in the following examples.

EXAMPLE 1

Figure 1:
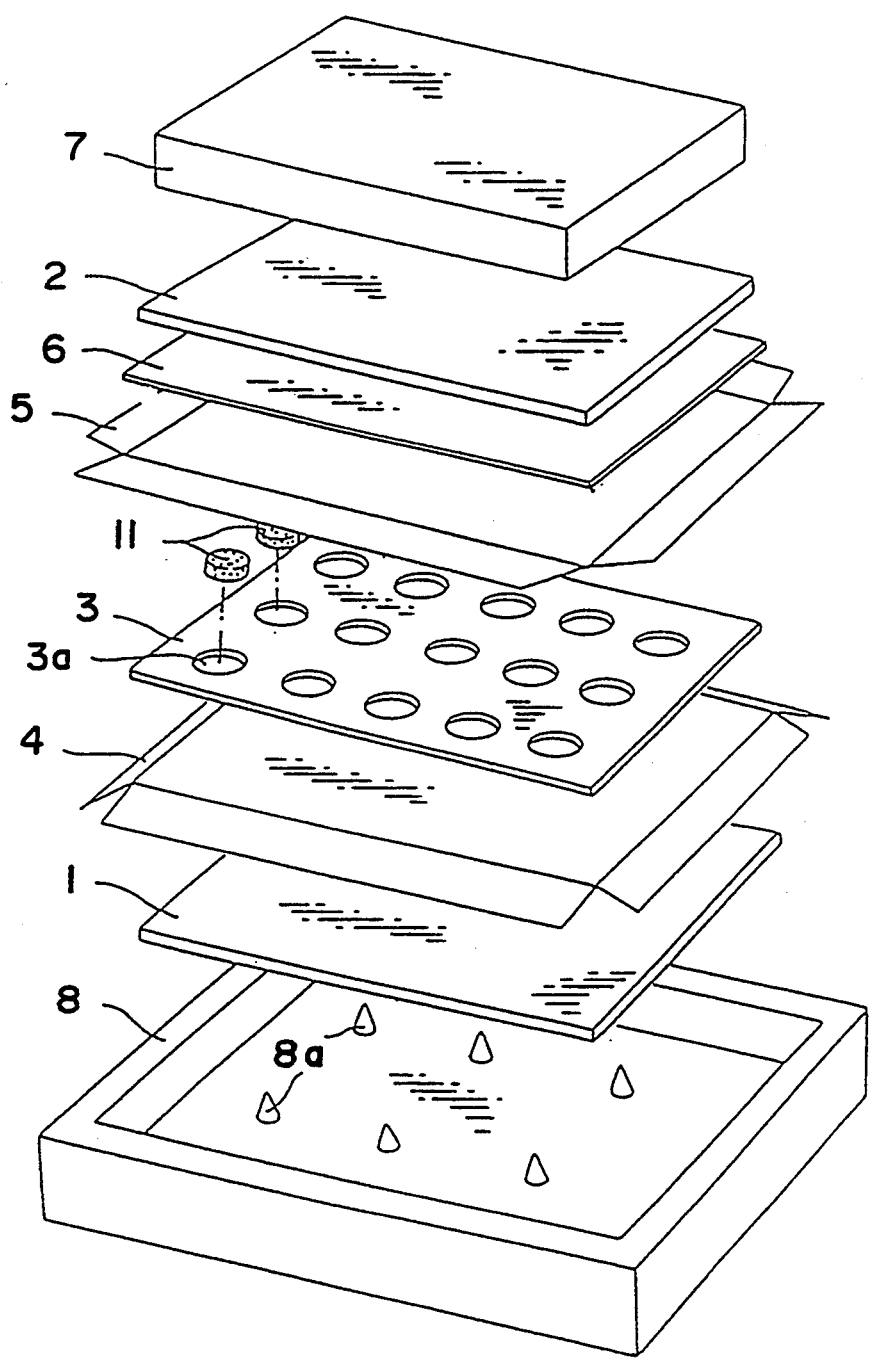
FIG. 1 is an exploded perspective side view indicating an example of the radiation measurement according to the present invention.

FIGS. 1 and 2 show an example of a method for radiation measurement according to the present invention. FIGS. 2(A) to (C) are cross sectional views along line II—II of FIG. 1. FIG. 2(A) shows a condition before the sample is compressed to a fixed thickness, FIG. 2(B) shows the condition wherein a sample is spread to the fixed thickness, FIG. 2(C) shows the condition wherein the sample spread to the fixed thickness is frozen. The procedure of radiation measurement will be illustrated in connection with the accompanying drawings.

To spread the sample to a fixed thickness, two thick stainless steel plates 1, 2 and a lead block 7 are used as shown in FIGS. 1 and 2. The stainless steel plates 1 and 2 (hereinafter referred to as a base plate 1 and a top plate 2, respectively) are 5 mm thick and both of their upper and lower surfaces are flat. The top plate 1 is covered with polyvinylidene film 4, which does not have wrinkles.

Figure 2A:
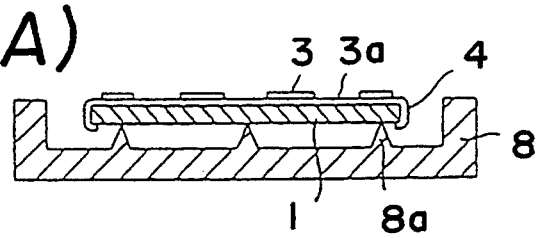
FIGS. 2(A) to (F) are cross sectional views indicating each step of the example of the radiation measurement according to the present invention.
Figure 2B:
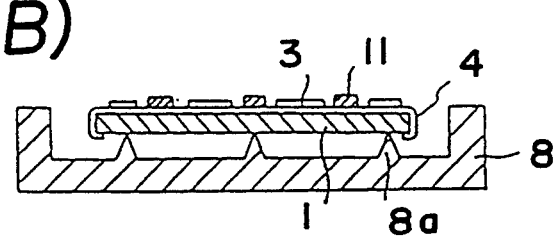

As shown in FIG. 2(A), the top plate 1 is placed flat on a support 8a attached on the base of a foaming polystyrol tray 8, and spacers 3 are placed on the top plate 1 covered with the film 4. The spacers 3 are polystyrene films of 0.4 mm thickness, having 24 circular windows with a diameter of 24 mm, arranged in three lines and eight columns. As shown in FIG. 2(B), a biological sample 11 containing radioactive labeled substance is spread as flat as possible to assume a circle within the window 3a of the spacer 3. The biological sample 11 is a liquid or previously liquefied biological sample.

Figure 2C:
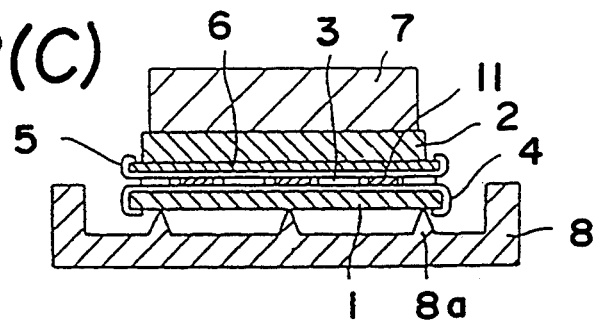

As shown in FIG. 2(C), the spacer 3 and the samples 11 in the window 3a are covered with a polyvinylidene chloride film 5 (thickness: 10 micron). On the film, the top plate 2 is placed with cardboard 6 interposed, on which is further placed a lead block 7. Then the biological samples 11 are spread to 0.4 mm in thickness, which is equivalent to the thickness of the spacer 3.

Figure 2D:
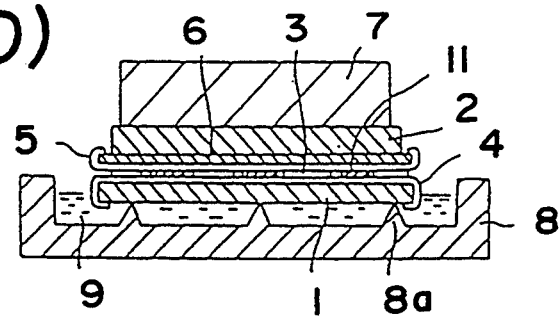

As shown in FIG. 2(D), liquid nitrogen 9 is poured in the foaming polystyrol tray 8 so that the base plate 1 is submerged to half of its thickness, thereby freezing the biological sample 11.

Figure 2E:
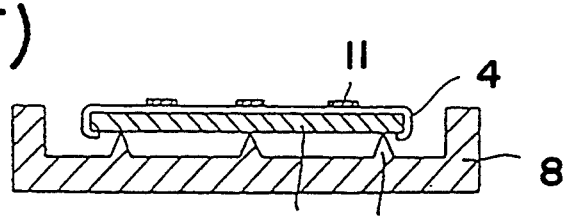

After the biological sample 11 is frozen, the lead block 7, the top plate 2, the film 5, the cardboard 6, and the spacer 3 are successively removed as shown in FIG. 2(E). In this case, the thin section of the frozen biological sample 11 does not adhered to the film 5 but to the film 4 on the base plate 1. The margin of the film 4 extending out of the base plate 1 is cut off and the film 4 is adhered to another mount 12 in a freezer at $-10°$ C.

Figure 2F:
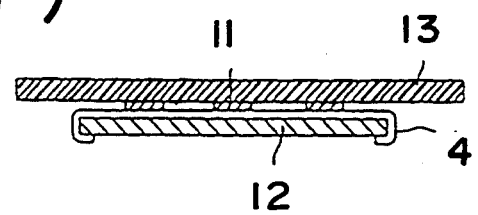

As shown in FIG. 2(F), the imaging plate 13 which has been cooled in a freezer is placed in contact with the mount 12 on which the sample 11 is placed with a protective film (not shown) interposed in a dark chamber. The imaging plate 13 utilizes photostimulated luminescence (PSL) and constitutes a part of the FUJIX Bio-imaging Analyzer BAS 2000 (manufactured by Fuji Photo Film Co., Ltd.). After contacting for 24 hours, the imaging plate 13 was separated from the mount 12 and the film 4, scanned with a laser, PSL emission was measured and the data were processed by a computer.

MEASUREMENT EXAMPLE 1

An example of radiation measurement according to the method of Example 1 is shown. An aqueous solution of [U-$^{14}$C] glucose (specific radioactivity: 10.7 GBq/mmol)(concentration: 100 microCi/cc) was appropriately diluted and injected into the caudal veins of male rats (5 microCi/100 g weight, 185 kBq; 10 microCi, 370 kBq; 20 microCi, 370 kBq) and the rats were killed after 10 minutes. The brain, liver, kidney, skeletal muscles and blood were collected (about 50 mg, each). The samples other than blood were liquefied by the following method.

To about 50 mg of the sample, twice the volume of 20% gelatin solution and the same volume of 2N KOH were added. After heating at 60° C. for 16 hours, four times the volume of 30% gelatin solution was added and the mixture was vigorously stirred.

According to Example 1, the above liquefied sample (14 microliters) was placed in the window 3a of the spacer 3 (0.4 mm thick) on the base plate 1 covered with the film 4 (polyvinylidene chloride film of 10 micrometer thick), which was covered with the film 5. Further, cardboard 6 and the top plate 2 were mounted. The sample 11 was slightly pressed with the lead block 7 placed on the top plate, spreading the sample between the films 3 and 4. Subsequently, the base plate 1 was cooled to about $-70°$ C. with liquid nitrogen according to Example 1 to freeze the biological sample 11, then the temperature of the base plate 1 was gradually raised to about $-20°$ C. The biological sample 11 was spread to a disk of 7 mm in diameter within the window 3a.

After 5 minutes, the lead block 7, the top plate 2, the cardboard 6, the film 5 and the spacer 3 were successively removed, and the film 4 on which the sample was placed was separated and transferred onto the mount 12, and a radiation measurement was carried out according to the procedure of Example 1 the using the FUJIX Bio-imaging Analyzer BAS 2000 (manufactured by Fuji Photo Film Co., Ltd., hereinafter referred to as Analyzer).

Figure 3:
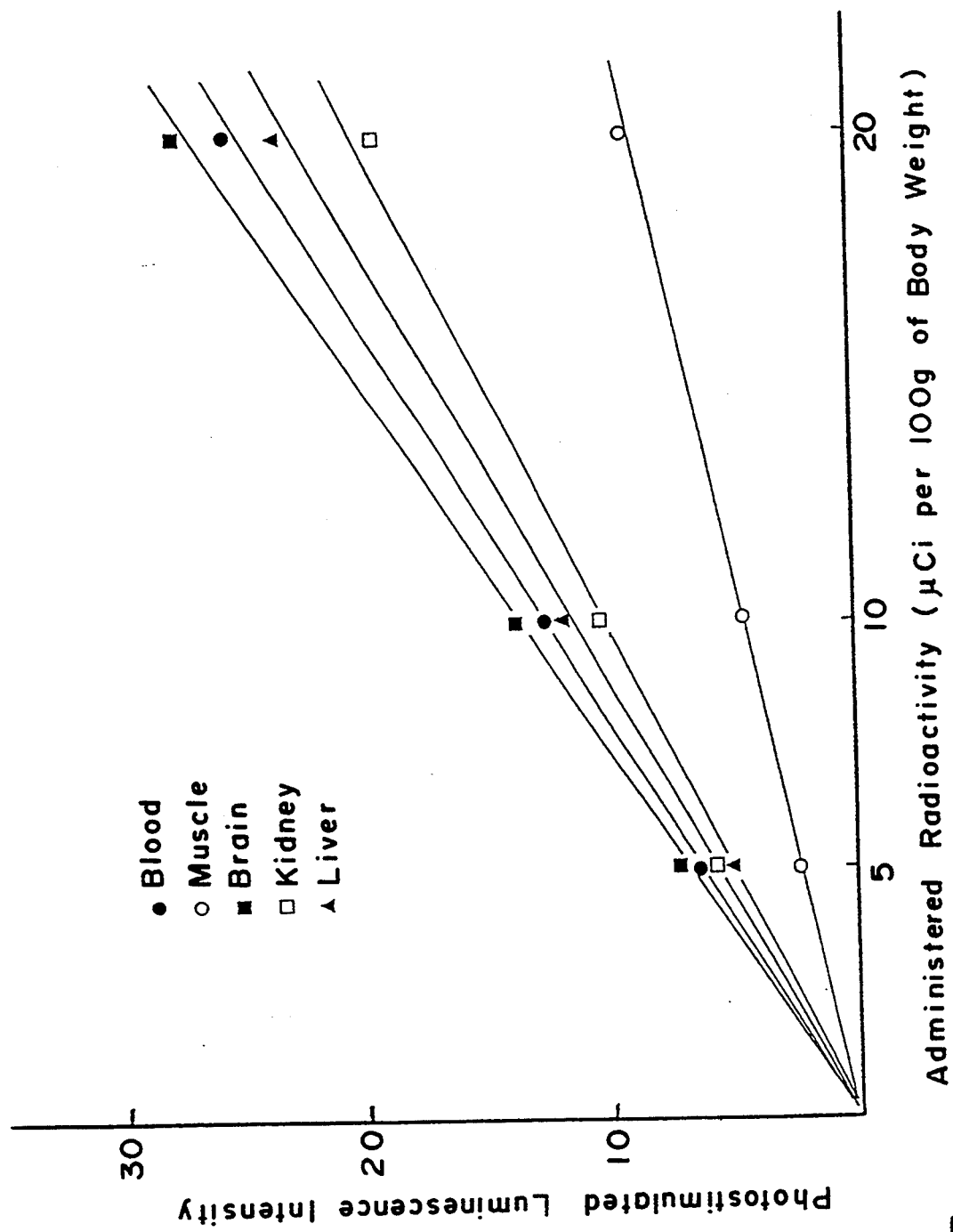
FIG. 3 is a graph showing results of the measurement of the example of radiation measurement according to the present invention.

The results of measurements are shown in FIG. 3. In FIG. 3, the abscissa indicates the administered radioactivity and the ordinate indicates the intensity of the photostimulated luminescence intensity (the intensity per unit area, background subtracted) measured by the Analyzer. For all samples, a good linear relation was found between the administered radioactivity and the emission intensity.

COMPARATIVE EXAMPLE 1

Fifty milligrams of the same tissue and blood samples as those in Example 1 were collected. Alkaline solubilizing agent (0.2 cc) was added to each sample in a vial for liquid scintillation, which was heated at 37° C. overnight, then dioxane scintillator solution (10 cc) was added. After sufficient emulsification, radioactivity of each sample was measured by an automatic three channel liquid scintillation counter equipped with an automatic quenching compensator.

Figure 4:
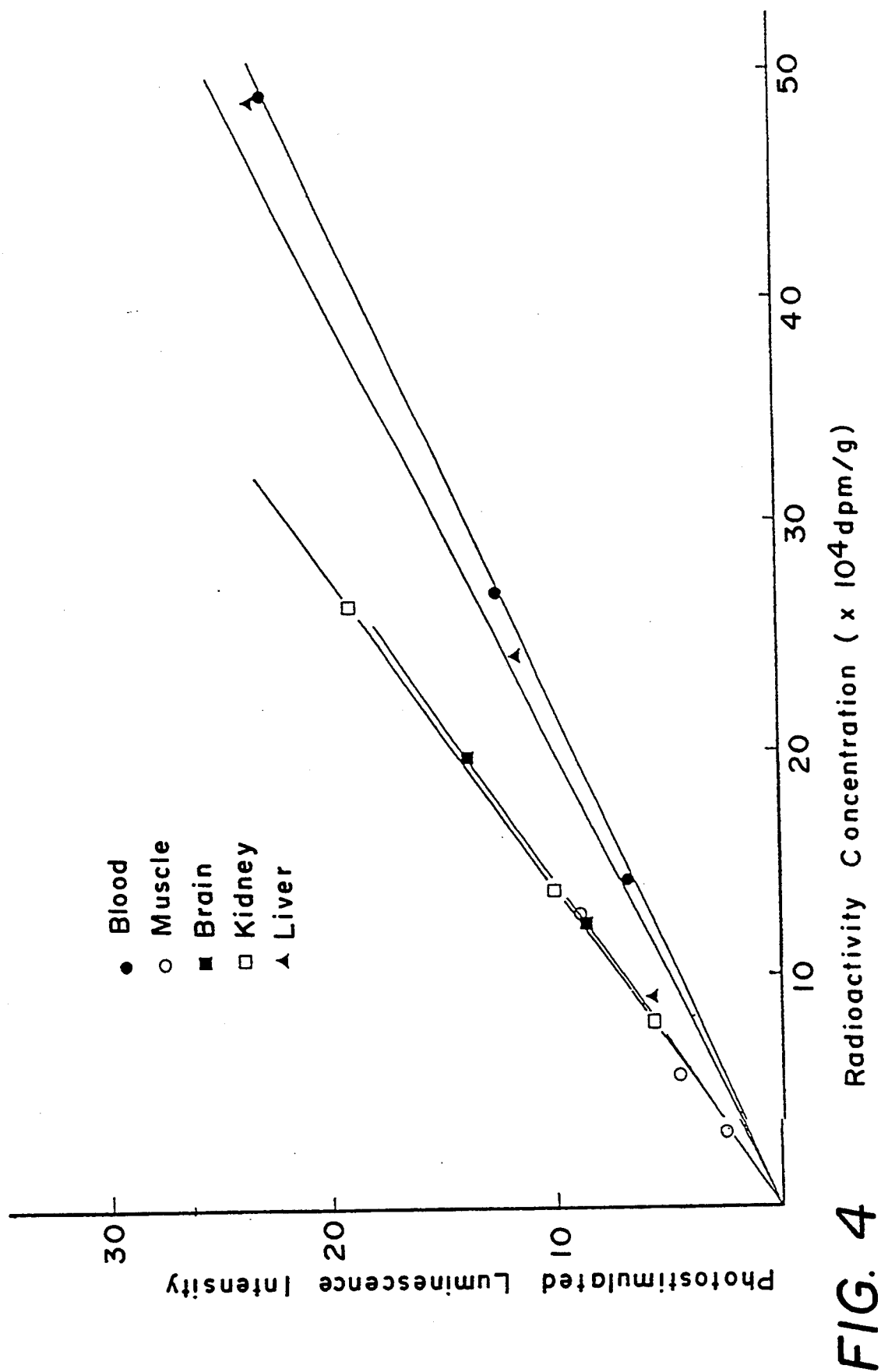
FIG. 4 is a graph comparing the radiation measurement in an example of the present invention and that by the conventional liquid scintillation counting method and showing a correlation between them.

The results of the liquid scintillation counting method in Comparative Example 1 and the results of the measurement in Example 1 are compared in the graph in FIG. 4. In FIG. 4, the abscissa indicates the radioactivity concentration according to a liquid scintillation counting method, and the ordinate indicates photostimulated luminescence intensity measured by the Analyzer.

FIG. 4 shows that good correlations are observed between the measurement by the liquid scintillation counting method and the measurement according to the present invention for blood, lung, kidney, brain and liver.

EXAMPLE 2

Soft solid samples such as organs were used in Example 2 as biological samples 11 instead of liquid or liquefied samples used in Example 1. The weight of the lead block 7 was sufficient enough to crush the sample between the base plate 1 and the top plate 2 under the pressure of about 5 g/cm$^2$. Freezing and radiation measurement were carried out in the same manner as in Example 1.

MEASUREMENT EXAMPLE 2

An example of radiation measurement according to the method of Example 2 is shown. An aqueous solution of [U-$^{14}$C] glucose (0.2 mCi/cc) was injected into the caudal veins of male rats (5 microCi/100 g weight, 185 kBq; 10 microCi, 370 kBq; 20 microCi, 370 kBq) and the rats were killed after 5 minutes. The brain, liver, kidney, skeletal muscles and blood were collected (about 50 mg, each). The samples other than blood were chopped finely into gruel with a knife or a spatula.

The above sample (about 50 mg) was placed in the window 3a of the spacer 3 (thickness: 0.2 mm) on the base plate 1 covered with the film 4 (polyvinylidene chloride film of 10 micrometer thick), on which were placed a cardboard 6 and the top plate 2 covered with the film 5. Further, the sample 11 was spread between the films 3 and 4 with the lead block 7 under a pressure of about 5 g/cm$^2$. Subsequently, the base plate 1 was cooled to about $-70°$ C. with liquid nitrogen in the same manner as in Example 1 to freeze the biological sample 11, then the temperature of the base plate 1 was gradually raised to about $-20°$ C. After freezing, radioactivity was measured in the same manner as in Example 1.

Figure 5:
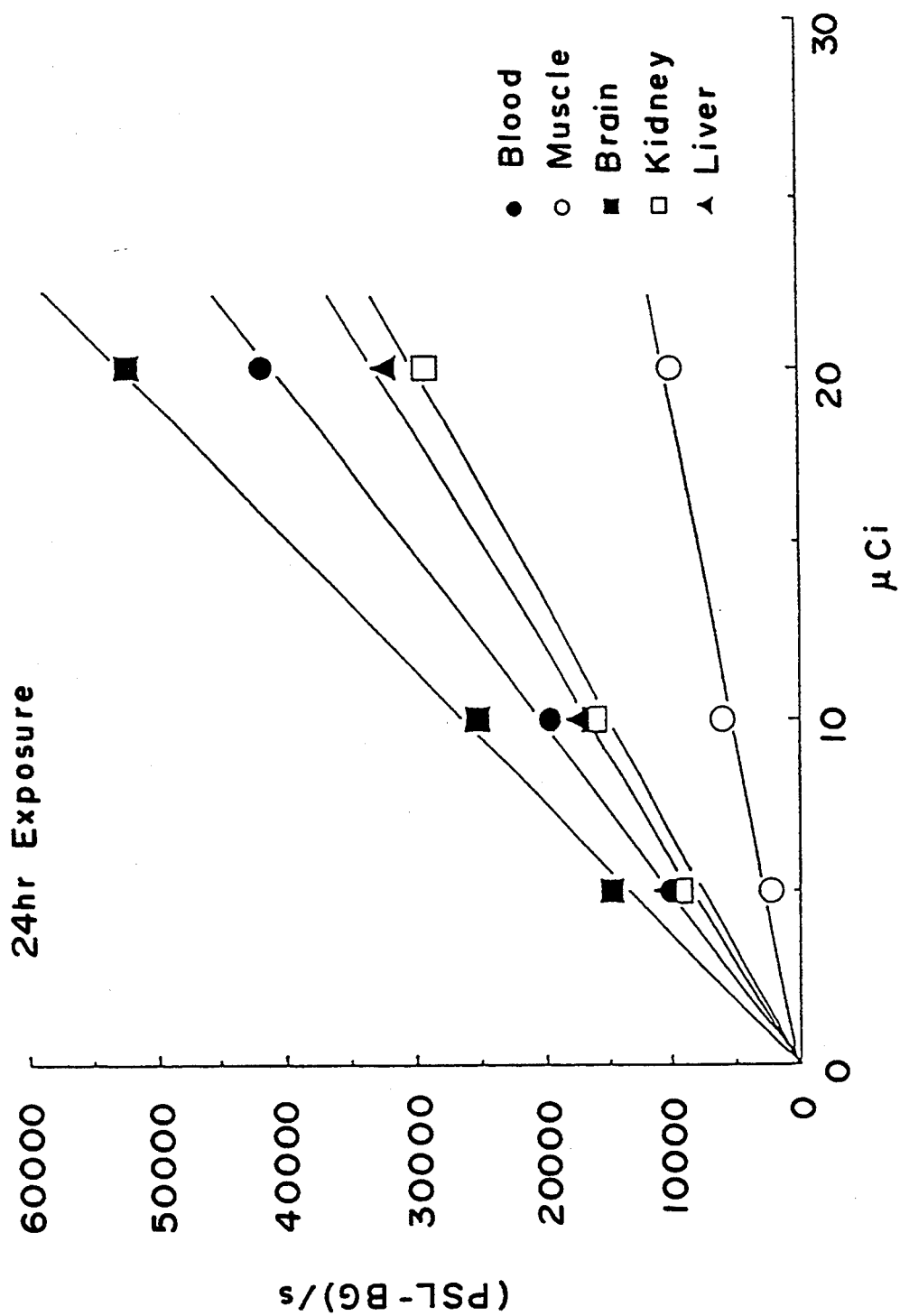
FIG. 5 is a graph showing results of another measurement example according to the present invention.

The results of the measurement are shown in FIG. 5. In FIG. 5, the abscissa indicates the administered radioactivity and the ordinate indicates the intensity of the photostimulated luminescence emission intensity (intensity per unit area from which background is subtracted, expressed as (PSL-BG/s) in the figure) measured by the Analyzer. For all samples, a good linear relation was found between the administered radioactivity and the emission intensity.

COMPARATIVE EXAMPLE 2

Fifty milligrams of the same tissue and blood samples as those in Example 2 were collected. Alkaline solubilizing agent (0.5 cc) was added to each sample in a vial for liquid scintillation, which was heated at 37° C. overnight, then dioxane scintillator solution (15 cc) was added. After sufficient emulsification, radioactivity of each sample was measured by an automatic three channel liquid scintillation counter equipped with an automatic quenching compensator.

Figure 6:
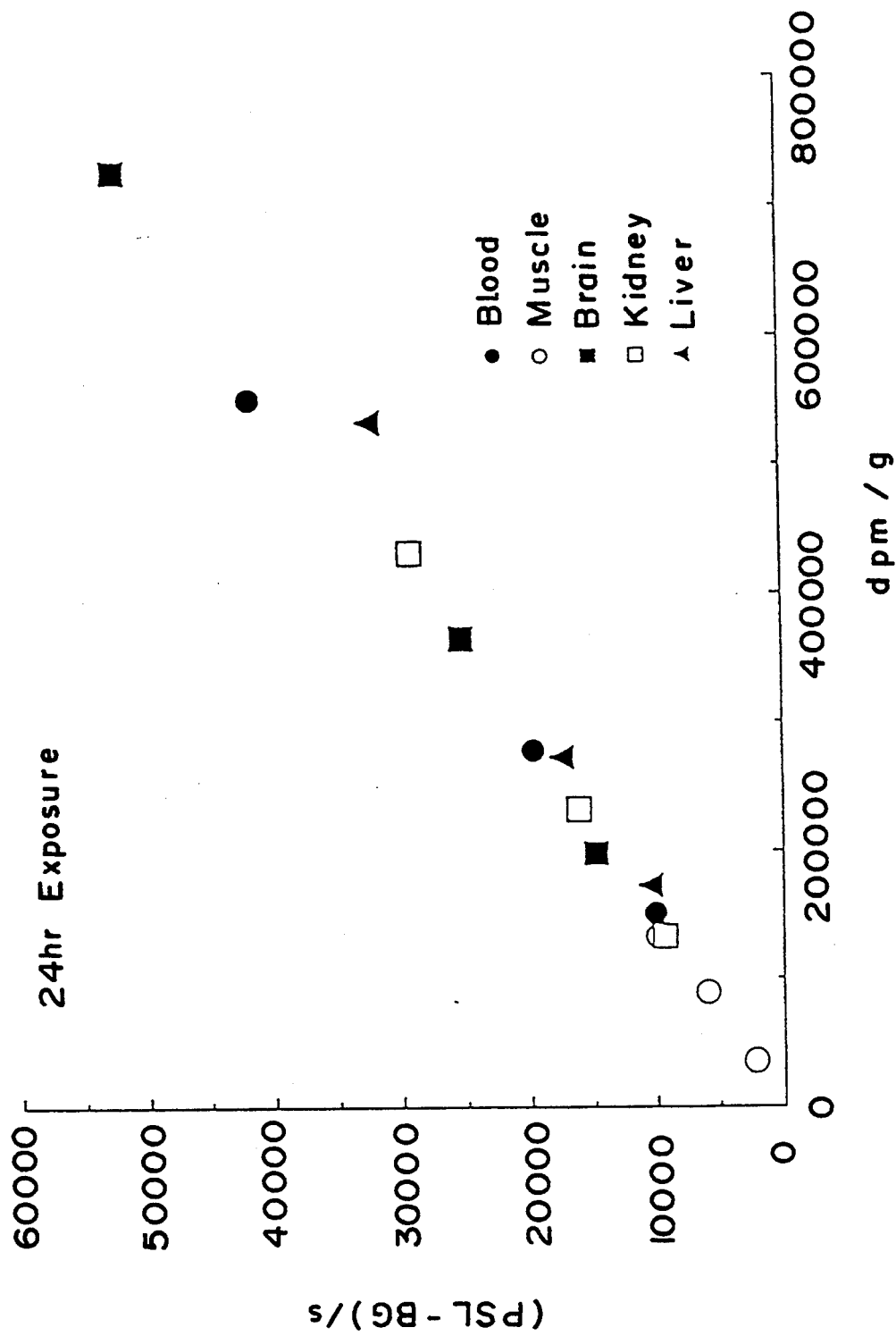
FIG. 6 is a graph showing a correlation between the radiation measurement according to the present invention and that by the conventional liquid scintillation counting method.

The results of the liquid scintillation counting method in Comparative Example 2 and the results of the measurement in Example 2 are compared in the graph in FIGS. 6. In FIG. 6, the abscissa indicates the radioactivity concentration (unit: dpm/g) according to the liquid scintillation counting method, and the ordinate indicates photostimulated luminescence intensity measured by the Analyzer.

As shown in FIG. 4, within the range from 200,000 to 800,000 dpm/g, a good correlation was observed between the radioactivity measured by the present method and the radioactivity measured by liquid scintillation method for blood, lung, kidney, brain and liver.

EXAMPLE 3

Figure 7:
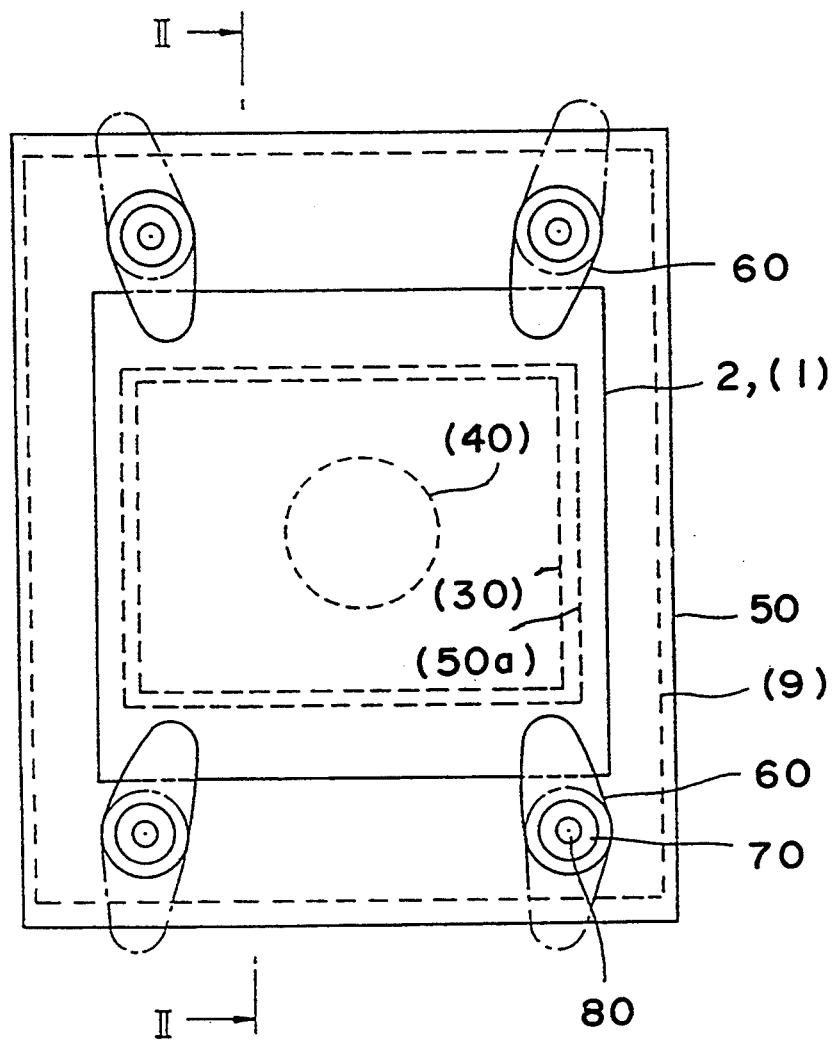
FIG. 7 is a top view of an example of a device for preparing samples for radiation measurement according to the present invention.
Figure 8A:
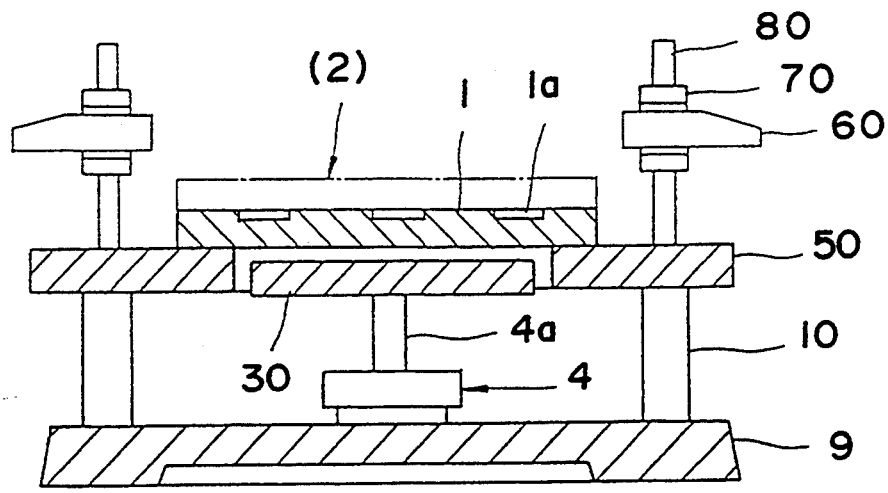
FIG. 8(A–C) a cross sectional view of an example of a device for preparing samples for radiation measurement according to the present invention.
Figure 8B:
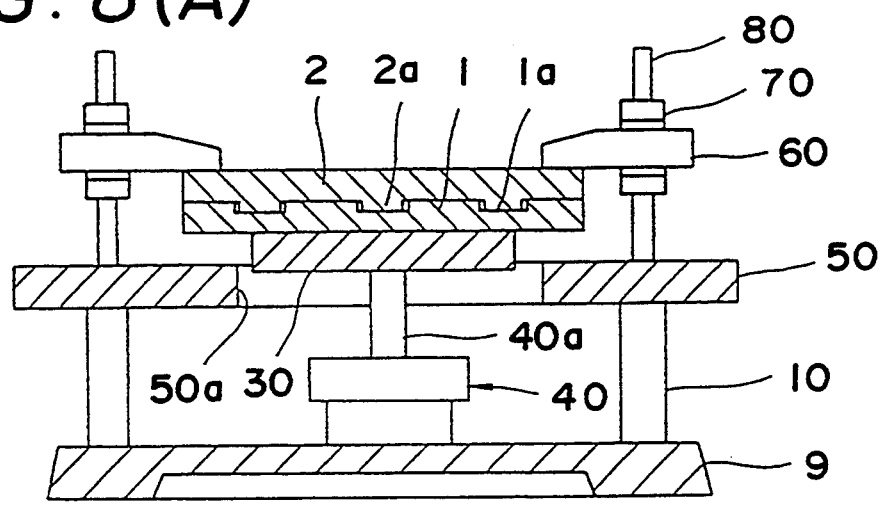
Figure 8C:
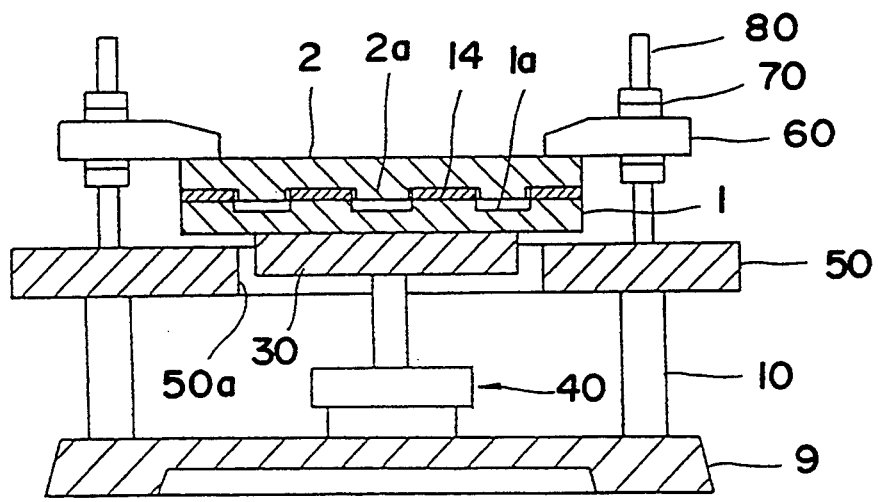

FIGS. 7 and 8 show an example of a method and a device for practical application of the method according to the present invention. FIGS. 8(A) to (C) show cross sectional views along line II—II of FIG. 7. FIG. 8(A) shows a condition in preparation before compression of the sample, FIG. 8(B) shows the condition wherein a sample wrapping film is pressed onto the sample, FIG. 8(C) shows the condition wherein the sample is pressed. In these figures, the sample wrapping film is not shown.

In FIGS. 7 and 8, the device for preparation of the sample for radiation measurement is provided with two thick stainless steel plates 1 and 2 to compress the frozen sample, a lift 30 and a stopper 60 to press these planes. The stainless steel plane 1 (hereinafter referred to as a base plate) has the upper and the lower surfaces which are flat and parallel to each other except for sample holes 1a on the upper surface. Each samples hole 1a has a circular section with a diameter of 12 mm and a depth of 2 mm, and the bottom is flat and parallel to the upper surface. The stainless steel plate (hereinafter referred to as a top plate 2) also has the upper and the lower surfaces which are flat and parallel to each other except for a protrusion 2a on the lower surface, and the lower surface closely contacts with the upper surface of the top plate 1. The protrusion 2a on the lower surface has a circular section of 11.6 mm diameter and may fit in the sample hole 1a. The height of the protrusion 2a on the lower surface is equal to the depth of the sample hole 1a. The sample holes 1a, 48 in total, are arranged in 6 lines and 8 columns. The protrusions 2a are arranged in the same manner. As shown in FIG. 8(A), the top plate 1 is initially placed on a table 50. The table 50 is fixed above the frame 9 with a support 10.

The table 50 has an opening 50a at the center which is smaller than the top plate 1. The lift 30 connected to a hydraulic device 40 by means of a coupling rod 40a can move vertically through the opening 50a. The table 50 and the hydraulic device 40 are fixed on the frame 9. Rigid shafts 80 are provided at the four corners of the table 50, and stoppers 6 are rotatably connected to the top of them by means of bearings 7. As shown in FIG. 8(B), when the stopper 60 is rotated inwards, the lower surfaces oppose the upper surface of the top plate 2. When the base plate 1 and the top plate 2 are pushed up by the lift 30 the lower surface of the stopper 60 contacts the upper surface of the top plate 2 to stop rising. In this case, the top face of the protrusion is contacts the base of the sample hole 1a. As shown in FIG. 8(C), a spacer 14 having a window with the same shape as that of the sample hole 1a is placed between the base plate 1 and the top plate 2, providing a space between the base of the sample hole 1a and the protrusion 2a.

The procedure for preparation of a sample for radiation measurement using a device as shown in FIGS. 7 and 8 will be illustrated with reference to FIGS. 9(A) to (E).

The hydraulic device 40 is stopped, when the lift is located at the bottom dead point, and the base plate 1 is placed on the fixed point on the upper surface of the table 50. As shown in FIG. 9(A), a polyvinylidene chloride film 11 (thickness: 10 micron) is placed on the base plate 1, and the top plate 2 is placed on the film in such a way that protrusions 2a may extended into the sample holes 1a.

When the hydraulic device 40 is operated and the lift is raised, the base plate 1 and the top plate 2 are simultaneously raised and the top plate 2 is stopped as its upper surface contacts with the lower surface of the stopper 60. In this case, the film 11 between the base plate 1 and the top plate 2 are forced into the sample hole 1a as shown in FIG. 9(B).

The hydraulic device 40 is stopped and the lift 30 is descended to bring the base plate 1 and the top plate 2 back to the original positions. Subsequently, the top plate 2 is removed. The film 11 remained adhering onto the internal surface of the sample hole la.

As shown in FIG. 9(D), the biological sample 13 which has been frozen in a freezer and contains radioactive labeled material is mounted on the film 11 as smoothly as possible in the sample hole 1a, which is covered with the polyvinylidene chloride film 12 (thickness: 10 micron) flatly without forming wrinkles as shown in FIG. 9(E). On the film 12, spacers 14 are mounted smoothly in such a way that the window registers the sample hole 1a, on which the top plate 2 is placed so that the protrusion 2a is opposed to the sample hole 1a.

The hydraulic device 40 is operated again. When the lift is raised to push up the base plate 1, as shown in FIG. 9(F), the top plate 2 is stopped by the stopper 60, and the biological sample 13, placed between the films 11 and 12 between the base of the sample hole 1a and the protrusion 2a, is crushed. Because of the existence of the spacer 14 between the upper surface of the base plate 1 and the top plate 2, there is a space left in the bottom of the sample hole 1a, the depth of which is equivalent to the thickness of the spacer 14. Accordingly, the biological sample 13 may not be compressed to the thickness less than this height, and crushed to a constant thickness.

Figure 10:
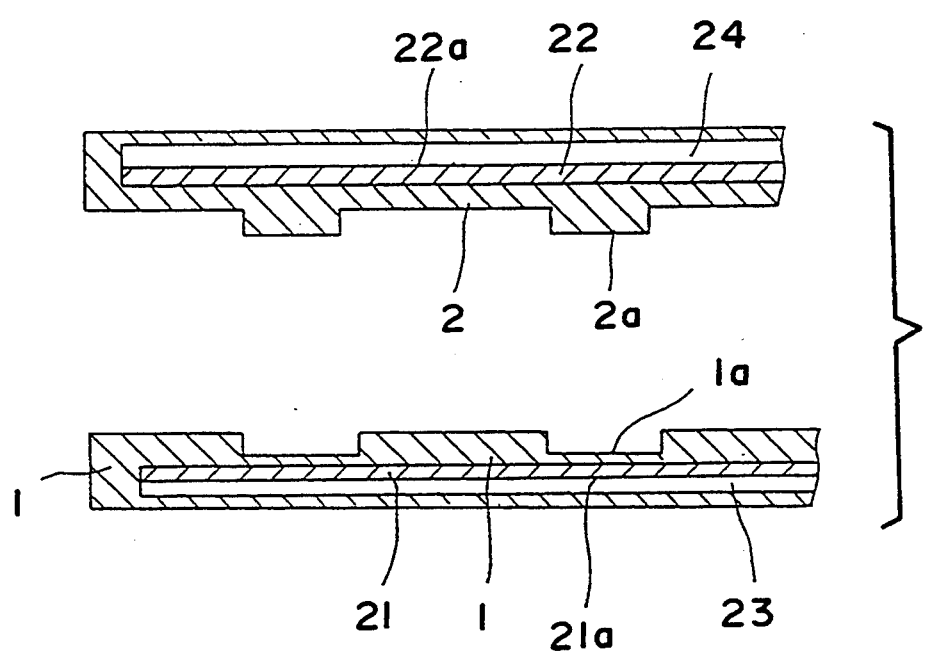
FIG. 10 is a cross sectional view of the part of the device shown in FIGS. 1 and 2.

Although not shown in FIGS. 7 to 9, the base plate 1 and the top plate 2 are respectively provided with built-in cooling elements 21 and 22 utilizing a Peltier effect as shown in FIG. 10. Accordingly, they are cooled to the required temperature and the biological sample 13 between them can be kept frozen. Cooling water for heat radiation is passed through the jackets 23 and 24 contacting with the heat radiating surfaces of the cooling elements 21a and 22a.

EXAMPLE 4

Figure 11:
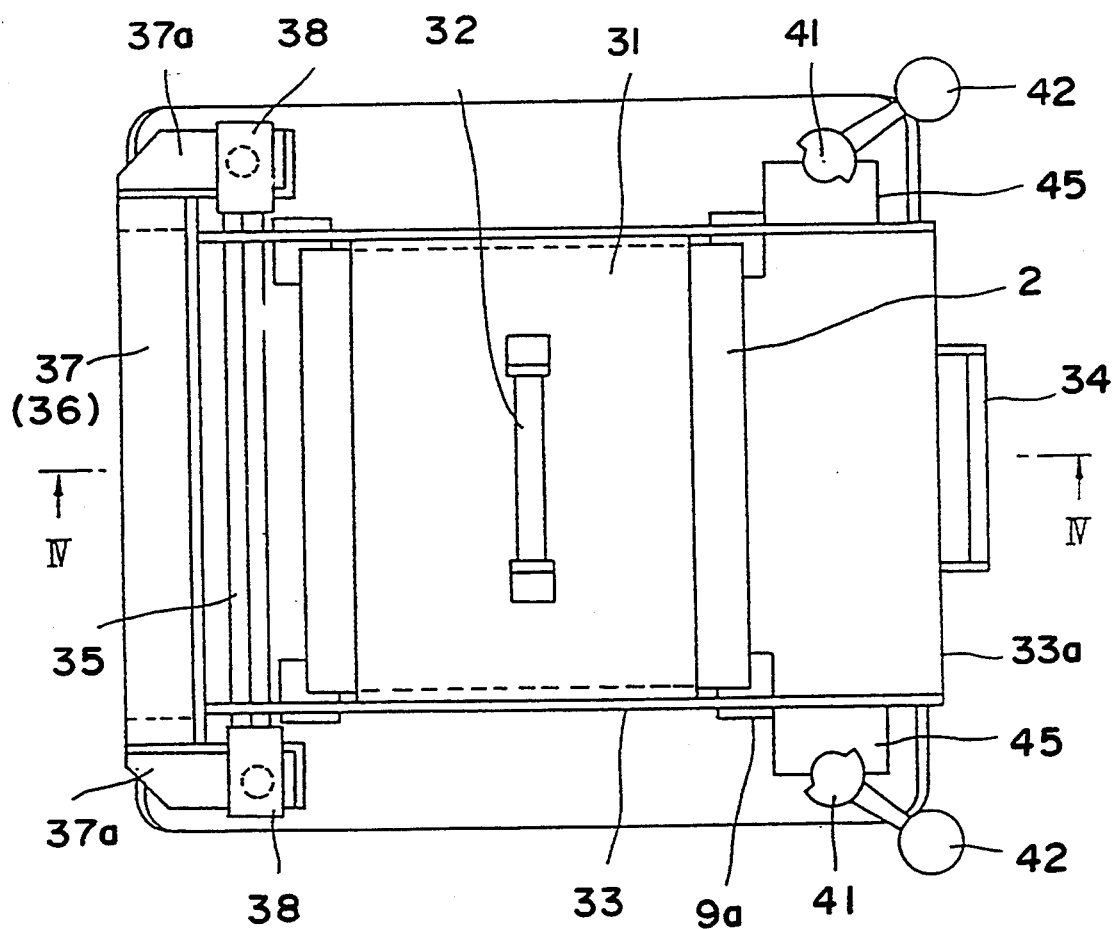
FIG. 11 is a top view of another example of a device for preparing sample for radiation measurement according to the present invention.

Another example of the device for preparing a sample for radiation measurement according to the present invention is shown in FIGS. 11 and 12. The base plate 1, the top plate 2, the sample hole 1a, the protrusion 2a and the spacer 14 are the same as those in Example 3. The upper surface of the frame 9 is flat and the stainless steel plate 1 (a base plate) is placed on the area surrounded by the guides 9a. The guide 9a is an L-shaped protrusion. On the stainless steel plate 2 (a top plate), a pressure plate 31 fixed to the housing 33 is placed. A handle 32 is attached to the pressure plate 31, a handle 34 to the first transition 33a of the housing 33. The rear portion of the housing 33 is mounted on the supporting rod 35 having a triangle section. The supporting rod 35 is energized upwardly. The last transition 36 of the housing 33 serves as a stopper push plate, and is contacted with the rear stopper 37 by energization of the supporting rod 35. The height of the rear stopper 37 can be adjusted by a means not shown in the figure. Energization of the supporting rod 35 is afforded by means of the L-shaped supporting device 38 by a spring 39 provided on the upper part of the support 10. Such energization is sufficient enough to generate a pressure of more than 100 g/cm² which is required for crushing the sample between the base of the sample hole 1a and the protrusion 2a of the top plate 2.

Rotable stoppers 41 having semicircular cams are provided on the top of the forward support 10. The cams bite from above with the perimeter of the semicircular notch of the gear fixed on the front face of the above housing 33 to lock the device 45 and to prevent upward movement of the housing 33 and control its height. The stopper 41 is operated by the lever 42.

The operation of the device shown in FIGS. 11 and 12 will be explained.

Figure 12A:
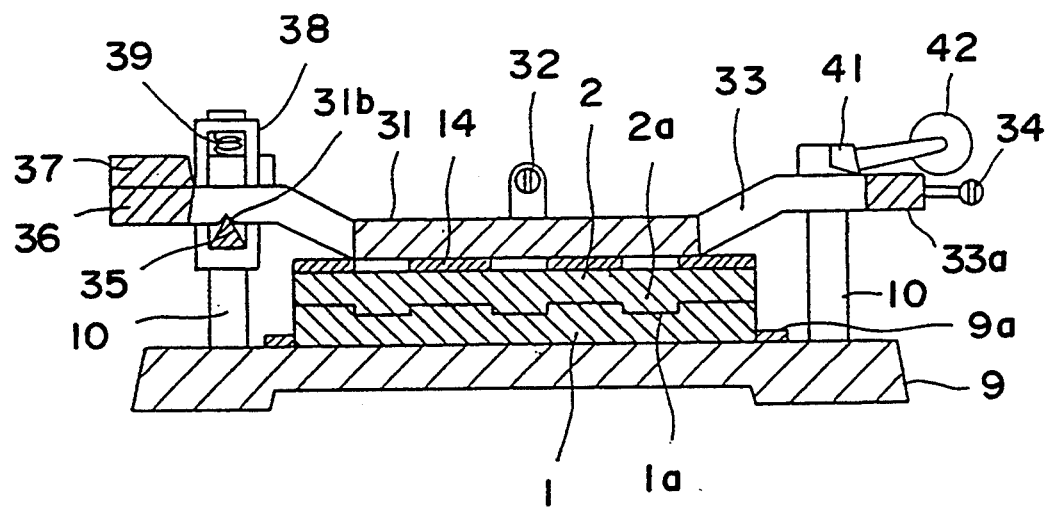
FIG. 12(A–B) is a cross sectional view of a device for preparing sample for radiation measurement according to the present invention.

Firstly, the base plate 1 is mounted on the frame 9. The lever 42 is rotated to the outer side to unlocked the stopper 41. The housing 33 as well as the pressure plate 31 are removed and the top plate 2 is mounted on the base plate 1 with thin plastic film inserted between them in the same manner as in Example 1, on which is further placed the spacer 14. The pressure plate 31 is pushed up using the handle 32 while the last transition 36 of the housing 33 is inserted beneath the stopper 37 and the channel 33b of the rear part of the side is contacted with the supporting rod 35, the pressure plate 31 descending above the spacer 14. When the handle 32 is released, the pressure plate 31 descends upon the spacer 14 by its empty weight. In this case, the rear portion of the housing 33 is energized upwardly by the spring 39 by means of a supporting rod 35. Accordingly, the last transition 36 contacts the stopper 37 and the pressure plate 31 closely contacts the spacer 14 (slightly pushing up the lever 34 as needed) as shown in FIG. 12(A). Under such conditions, the lever 42 is rotated to the inner side to lock the device 45 (FIG. 11) by biting with the cam of the stopper 41. The base plate 1, the top plate 2, the spacer 14, the the pressure plate 31 are closely contacted and fixed. The height of the stopper 37 is adjusted so that the pressure plate 31 just contacts the last transition 36 of the housing 33 when the pressure plate 31 is closely contacted with the spacer 14.

Figure 12B:
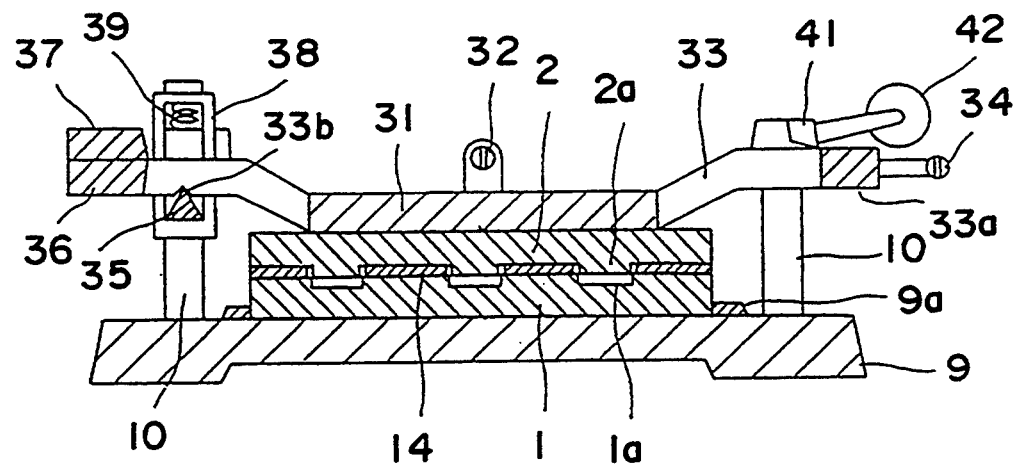

In this way, the film 11 is adhered to the bottom of the sample hole la as shown in FIG. 9(B). By the reverse operation, the pressure plate 31, the spacer 14, the top plate 2 are successively removed to obtain the condition shown in FIG. 9(C). The biological sample 13 which has been frozen in a freezer is placed on the film 11 in the sample hole 1a as shown in FIG. 9(D). As shown in FIG. 9(E), the film 11 and the biological sample 13 are covered with the thin film 12 (same type as the film 11), on which is placed the spacer 14 so that the window 14a registers the sample hole 1a. Then, the top plate 2 is placed. Except for the pressure plate 31 which is placed directly on the top plate 2, the above operation is repeated to adhere the pressure plate 31 to the top plates 2. Accordingly, the top plate 2, the spacer 14, the base plate 1 are adhered closely with one another as shown in FIG. 12(B), and the biological sample 13 is compressed to the thickness almost equal to that of the spacer 14 between the films 11 and 12 in the sample hole 1a, and sealed as shown is FIG. 9(F).

MEASUREMENT EXAMPLE 3

An example of a radiation measurement using a sample prepared utilizing a method and a device of the present invention will be illustrated. The device in Example 3 was pre-cooled for 30 minutes before usage and the top plate 2 and the base plate 1 were cooled to $-50°$ C. An aqueous solution of [methyl $^{14}$C] aminoantipyrine (100 microCi/cc, 0.1 cc) was administered to rats intravenously and the rats were killed after 30 minutes. The organs containing a relatively large amount of blood, the contents in the digestive tract and blood were collected from the dead body. Each sample was collected in the amounts of at least 3 grades selected from seven, i.e., 10, 20, 30, 50, 100 and 1000 mg, then frozen. A sheet of polyvinylidene chloride of 10 micrometer thick (film 11) was placed on the base plate 1 of the device of the Example 3, which is pressed by the top plate 2 to insert in the sample hole 1a to form fit to the bottom of the sample hole. The top plate 2 was raised and the above sample was placed on the film 11 in the sample hole 1a and covered again with the same type of the film 12. A spacer 14 with windows was placed on the film, then the sample was pressed with the top plate 2 from above and crushed under a pressure of not less than 100 g/cm². After crushing, the temperatures of the base plate 1 and that of the top plate 2 were slightly raised, that is, to about −10° C.

After 5 minutes, the top plate 2 was removed, and two sheets of the film (11, 12) containing the sample were removed. Radiation measurement were carried out according to the following procedure using the FUJIX Bio-imaging Analyzer BAS 2000 (manufactured by Fuji Photo Film Co., Ltd.). An imaging plate which had been previously cooled in a freezer closely contacted the films 11 and 12 containing the sample in a dark chamber. After contacting for 24 hours, the plate was separated from the sample sheet, scanned with a laser, and PSL emission was measured and the data were processed by computer.

The results of the measurement of the whole blood and the brain are shown in FIG. 13(A); the results of the blood plasma, lung, liver, kidney, bladder, contents in stomach in FIG. 13(B); the results of the measurement of the contents of the intestine and a part of the measurement of the whole blood, brain and liver in FIG. 13(C). In FIGS. 13(B) and (C), the intensity of the radioactivity of liver is shown as 1/10 of the measured value.

For all samples, good linear relations were observed between the sample amount and the intensity of the radioactivity.

COMPARATIVE EXAMPLE 3

A fixed amount of the part of the organ, tissue and contents were collected, to which were added an alkaline solubilizing agent (5 cc each) in vials for liquid scintillation, which were heated at 37° C. overnight, then dioxane scintillator solution (15 cc) was added. After sufficient emulsification, the radioactivity of each sample was measured by an automatic three channel liquid scintillation counter.

Figures 14A, 14B, 14C:
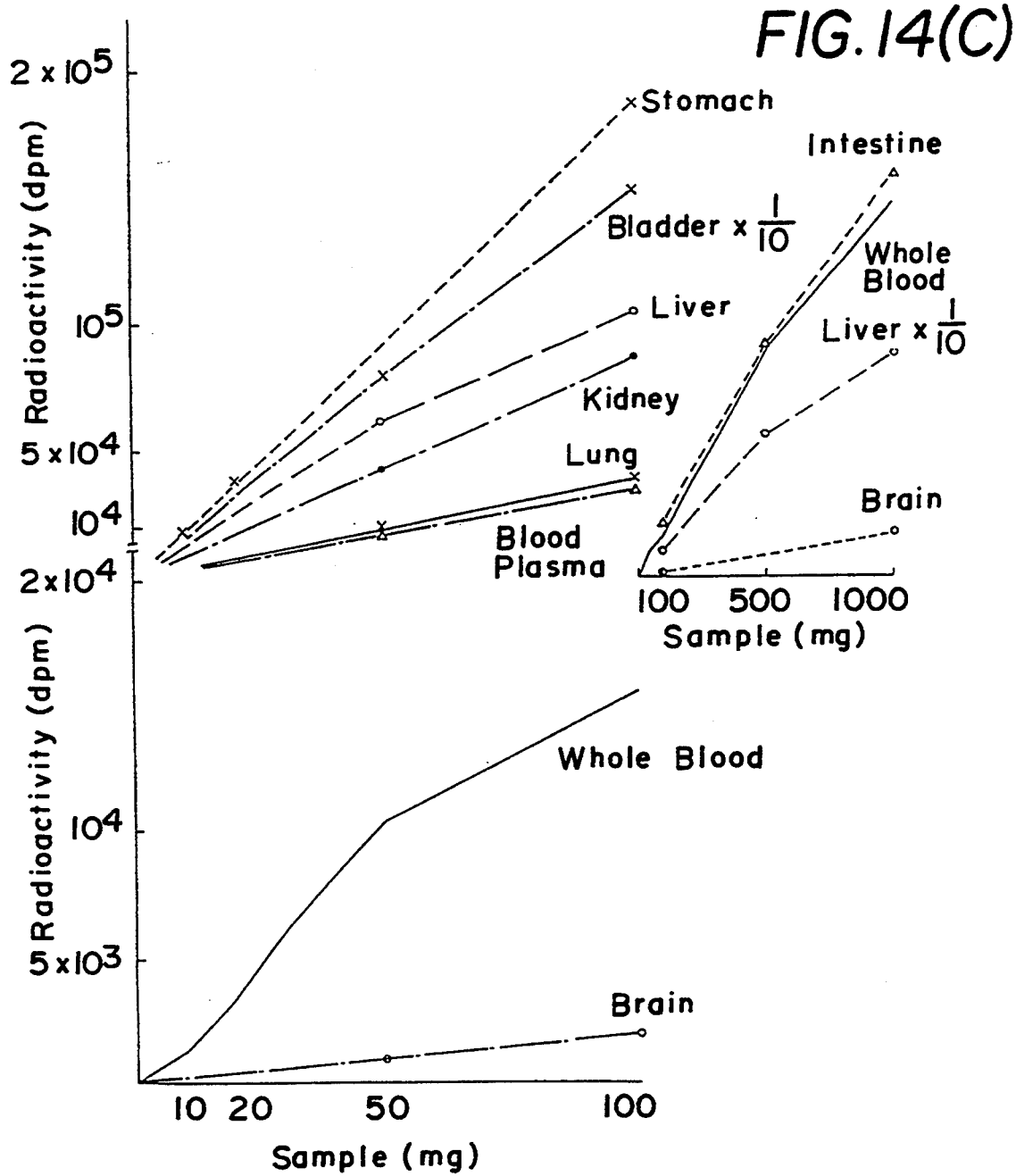
FIG. 14(A–C) is a graph showing a result of the measurement of radioactivity according to the conventional method.

The results of the measurement are shown in FIGS. 14(A) to (C), classified by the radioactivity level. Similar to FIG. 13, the radioactivity intensity of a bladder in FIGS. 14(B) and that of a liver in FIG. 14(C) are shown as 1/10 of the measured value.

Linear relations were observed for plasma, lung, kidney, brain and contents in stomach, but as for whole blood, liver, bladder and contents in intestine, the relations are far from linear.

The results of the Measurement Example and the Comparative Example show that the method for preparation of the sample according to the present invention provides results of radiation measurement with linear relation, which is superior to liquid scintillation method.

ADVANTAGE OF THE INVENTION

According to the method for radiation measurement of the present invention, a very small amount of the low-energy beta radioactivity in biological samples can be quantitatively measured without requiring complicated devices and labor. Further, no particular equipment nor labor for treatment of waste solution after measurement are required. Even in biological samples containing quenchers for scintillator, a very small amount of low-energy beta radioactivity can be quantitatively measured, in contrast to the liquid scintillation method, without requiring quencher correction. The method of the present invention can be applied not only to blood or other body fluids but to biological tissues which can hardly become homogeneous unless it is liquefied. Moreover, small organs which are difficult to handled as they are can be used as samples by liquefaction.

According to a method and a device for preparing samples of the present invention, samples for quantitative measurement of a very small amount of low-energy beta-radioactivity in biological sample can be prepared requiring no equipment and no labor. Moreover, no equipment and no labor for treatment of waste solution after measurement are required.

What is claimed is:

1. A method for radioactivity measurement of a water-containing biological sample which comprises: interposing a solid water-containing biological sample containing a β-ray emitting radioactive element between two substantially parallel planes facing each other at a predetermined distance such that opposite surfaces of said biological sample contact with said two planes, respectively, so as to have a uniform predetermined thickness; freezing said biological sample; and measuring β-ray radiation emitted from at least one of said surfaces of said biological sample while it contains water.

2. The method for radioactivity measurement according to claim 1, wherein said β-ray emitting radioactive element is selected from $^{14}C$ and $^{3}H$.

3. The method for radioactivity measurement according to claim 1, wherein said β-ray emitting radioactive element is contained in a radioactively labeled substance.

4. The method for radioactivity measurement according to claim 1, wherein said solid biological sample is pressed between two parallel flat surfaces of rigid bodies separated by a predetermined distance to form a tablet of uniform and predetermined thickness.

5. The method for radioactivity measurement according to claim 1, wherein said measurement of radioactivity is carried out by measuring intensity of photostimulated luminescence emitted according to the radioactivity.

6. A method for radioactivity measurement of a water-containing biological sample which comprises: interposing a liquid water-containing biological sample containing a β-ray emitting radioactive element between two substantially parallel planes facing each other at a predetermined distance such that opposite surfaces of said biological sample contact with said two planes, respectively, so as to have a uniform predetermined thickness; solidifying said biological sample; and measuring β-ray radiation emitted from at least one of said surfaces of said biological sample while it contains water.

7. The method for radioactivity measurement according to claim 6, wherein said β-ray emitting radioactive element is selected from $^{14}C$ and $^{3}H$.

8. The method for radioactivity measurement according to claim 6, wherein said β-ray emitting radioactive element is contained in a radioactively labeled substance.

9. The method for radioactivity measurement according to claim 6, wherein said liquid biological sample is spread between two parallel rigid planes separately by a predetermined distance to form a tablet of uniform and predetermined thickness.

10. The method for radioactivity measurement according to claim 9, wherein said tablet is further frozen.

11. The method for radioactivity measurement according to claim 6, wherein said measurement of radioactivity is carried out by measuring intensity of photostimulated luminescence emitted according to the radioactivity.

12. The method for radioactivity measurement of a water-containing sample according to any one of claims 6, 7, 8, and 9, wherein said solidifying is freezing.

13. The method for radioactivity measurement of a water-containing sample according to any one of claims 6, 7, 8, and 9, wherein said solidifying is accomplished by adding of gelatin and cooling.

14. The method for radioactivity measurement of a water-containing sample according to any one of claims 6, 7, 8, and 9, wherein said solidifying is accomplished by adding of gelatin followed by freezing.

15. A method for measurement of radioactivity of a $\beta$-ray emitting radioactive element contained in a water-containing biological sample which comprises:
- freezing a water-containing biological sample;
- uniformly pressing said frozen biological sample between two parallel flat surfaces of rigid bodies kept at a fixed temperature lower than the freezing point of said biological sample to form a tablet of predetermined thickness; and
- measuring the $\beta$-ray radioactivity of said tablet containing frozen water.

* * * * *